United States Patent
Johnson et al.

(10) Patent No.: US 12,144,909 B2
(45) Date of Patent: *Nov. 19, 2024

(54) BONE REPAIR COMPOSITION AND KIT

(71) Applicant: Zavation Medical Products, LLC, Flowood, MS (US)

(72) Inventors: Jeffrey Johnson, Flowood, MS (US); Nels J Lauritzen, Piscataway, NJ (US); Brent Mitchell, Haskell, NJ (US)

(73) Assignee: ZAVATION MEDICAL PRODUCTS, LLC, Flowood, MS (US)

( * ) Notice: Subject to any disclaimer, the term of this patent is extended or adjusted under 35 U.S.C. 154(b) by 143 days.

This patent is subject to a terminal disclaimer.

(21) Appl. No.: 17/136,584

(22) Filed: Dec. 29, 2020

(65) Prior Publication Data

US 2021/0113738 A1   Apr. 22, 2021

Related U.S. Application Data

(63) Continuation of application No. 16/230,399, filed on Dec. 21, 2018, now Pat. No. 11,090,412.

(51) Int. Cl.
| | |
|---|---|
| A61L 27/38 | (2006.01) |
| A61F 2/28 | (2006.01) |
| A61L 24/02 | (2006.01) |
| A61L 27/12 | (2006.01) |
| A61L 27/24 | (2006.01) |
| A61L 27/46 | (2006.01) |
| A61L 27/54 | (2006.01) |

(52) U.S. Cl.
CPC ............ *A61L 27/3847* (2013.01); *A61F 2/28* (2013.01); *A61L 27/12* (2013.01); *A61L 27/24* (2013.01); *A61L 27/54* (2013.01); *A61F 2002/2817* (2013.01); *A61L 24/02* (2013.01); *A61L 27/46* (2013.01); *A61L 2300/414* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,280,954 A | 7/1981 | Yannas et al. | |
| 4,947,840 A | 8/1990 | Yannas et al. | |
| 5,645,591 A | 7/1997 | Kuberasampath et al. | |
| 7,105,182 B2 | 9/2006 | Szymaitis | |
| 7,303,814 B2 | 12/2007 | Lamberti et al. | |
| 7,758,803 B2 | 7/2010 | Chang et al. | |
| 7,799,767 B2 | 9/2010 | Lamberti et al. | |
| 7,833,968 B2 | 11/2010 | Soo et al. | |
| 8,053,423 B2 | 11/2011 | Lamberti et al. | |
| 8,128,706 B2 | 3/2012 | Kaigler, Sr. | |
| 8,153,591 B2 | 4/2012 | Masters et al. | |
| 8,313,328 B2 | 11/2012 | Szymaitis | |
| 8,506,981 B1 | 8/2013 | Borden | |
| 8,567,162 B2 | 10/2013 | Bagga et al. | |
| 8,609,122 B2 | 12/2013 | Lamberti et al. | |
| 8,664,202 B2 | 3/2014 | Lamberti et al. | |
| 8,883,195 B2 | 11/2014 | Bagga et al. | |
| 8,957,050 B2 | 2/2015 | Lamberti et al. | |
| 9,163,212 B2 | 10/2015 | McKay | |
| 9,220,595 B2 | 12/2015 | Bagga et al. | |
| 9,301,816 B2 | 4/2016 | Kaigler, Sr. | |
| 9,320,601 B2 | 4/2016 | D'Agostino et al. | |
| 9,333,276 B2 | 5/2016 | Guelcher et al. | |
| 9,447,115 B2 | 9/2016 | Ting et al. | |
| 9,511,115 B2 | 12/2016 | Soo et al. | |
| 9,555,155 B2 | 1/2017 | Ganatra et al. | |
| 9,610,382 B2 | 4/2017 | Lamberti et al. | |
| 9,707,079 B2 | 7/2017 | Chang et al. | |
| 9,717,823 B2 | 8/2017 | McKay | |
| 9,737,634 B2 | 8/2017 | Okimura et al. | |
| 9,770,531 B2 | 9/2017 | Altschuler | |
| 9,789,225 B2 | 10/2017 | Bagga et al. | |
| 9,801,946 B2 | 10/2017 | Guelcher et al. | |
| 9,814,544 B2 | 11/2017 | Kaigler | |
| 9,839,722 B2 | 12/2017 | McKay | |
| 9,877,836 B2 | 1/2018 | Reves et al. | |
| 9,878,070 B2 | 1/2018 | Reves et al. | |
| 9,907,884 B2 | 3/2018 | Peters et al. | |
| 9,925,301 B2 | 3/2018 | Kaplan et al. | |
| 9,951,313 B2 | 4/2018 | Ingber et al. | |
| 9,974,534 B2 | 5/2018 | Troxel et al. | |
| 9,974,828 B2 | 5/2018 | Ting et al. | |
| 9,987,394 B2 | 6/2018 | Meretzki | |
| 9,993,346 B2 | 6/2018 | McCullen | |
| 9,999,705 B2 | 6/2018 | Masters et al. | |
| 10,004,806 B2 | 6/2018 | Szymaitis | |
| 10,010,609 B2 | 7/2018 | D'Agostino et al. | |
| 10,016,278 B2 | 7/2018 | Bradica et al. | |
| 10,022,231 B2 | 7/2018 | Estes et al. | |

(Continued)

OTHER PUBLICATIONS

Walsh et al. (PLoS One Jan. 3, 2017;12(1):e0168883).*
Medco bone graft implant tray product web page (2018). Obtained from <https://medcoinstruments.com/store/Implant-Tray-For-Bone-Grafting-Titanium-p16459496> on Mar. 24, 2023.*
Jun. 25, 2020, Interview Agenda for related U.S. Appl. No. 16/230,399 (eight (8) pages).

(Continued)

*Primary Examiner* — Patricia Duffy
*Assistant Examiner* — Garen Gotfredson
(74) *Attorney, Agent, or Firm* — IP & T GROUP LLP

(57) ABSTRACT

A biocompatible material for bone repair is described. The bone repair composition includes a mixture of a type I collagen, a type I collagen-glycosaminoglycan coprecipitate, tricalcium phosphate; and bioactive glass. Methods of using the composition for bone repair, and a kit for the bone repair composition are also described.

21 Claims, 3 Drawing Sheets

(56) References Cited

U.S. PATENT DOCUMENTS

| | | |
|---|---|---|
| 10,028,776 B2 | 7/2018 | D'Agostino et al. |
| 10,081,794 B2 | 9/2018 | Arinzeh et al. |
| 10,149,920 B2 | 12/2018 | Lao et al. |
| 10,149,923 B2 | 12/2018 | Carte |
| 10,160,785 B2 | 12/2018 | Cerovsky et al. |
| 10,207,027 B2 | 2/2019 | Nyemscek et al. |
| 10,227,713 B2 | 3/2019 | Ganatra et al. |
| 10,265,436 B2 | 4/2019 | Lamberti et al. |
| 10,279,078 B2 | 5/2019 | Cox et al. |
| 10,286,113 B2 | 5/2019 | Boden et al. |
| 10,328,103 B2 | 6/2019 | Wasielewski |
| 10,335,458 B2 | 7/2019 | Soo et al. |
| 10,335,516 B2 | 7/2019 | Bagga et al. |
| 10,350,049 B2 | 7/2019 | Morse et al. |
| 10,383,731 B2 | 8/2019 | Vickers |
| 10,383,981 B2 | 8/2019 | Lamberti et al. |
| 10,434,220 B2 | 10/2019 | Boden et al. |
| 10,448,944 B2 | 10/2019 | Marchand et al. |
| 10,470,885 B2 | 11/2019 | Bake et al. |
| 10,494,604 B2 | 12/2019 | Hans-Moore et al. |
| 10,500,312 B2 | 12/2019 | Bagga et al. |
| 10,507,020 B2 | 12/2019 | Limem et al. |
| 10,524,916 B2 | 1/2020 | Jie et al. |
| 10,537,577 B2 | 1/2020 | Boden et al. |
| 10,537,666 B2 | 1/2020 | Paddock et al. |
| 10,549,013 B2 | 2/2020 | Lao et al. |
| 10,590,566 B2 | 3/2020 | Ganatra et al. |
| 10,603,409 B2 | 3/2020 | McKay |
| 10,626,521 B2 | 4/2020 | Rizk et al. |
| 2002/0112981 A1 | 8/2002 | Cooper et al. |
| 2003/0193032 A1 | 10/2003 | Marshall |
| 2008/0187571 A1 | 8/2008 | Clineff et al. |
| 2010/0098673 A1* | 4/2010 | D'Antonio .............. A61L 27/46 424/549 |
| 2017/0209626 A1 | 7/2017 | Deev et al. |
| 2017/0232151 A1 | 8/2017 | Tuan et al. |
| 2017/0246353 A1 | 8/2017 | Yang et al. |
| 2017/0246355 A1 | 8/2017 | Preiss-Bloom et al. |
| 2017/0291932 A1 | 10/2017 | Safadi |
| 2017/0360912 A1 | 12/2017 | Lerouge et al. |
| 2018/0000987 A1 | 1/2018 | Yang et al. |
| 2018/0008746 A1 | 1/2018 | Bagga et al. |
| 2018/0028317 A1 | 2/2018 | Schlachter |
| 2018/0154047 A1 | 6/2018 | Reves et al. |
| 2018/0168813 A1 | 6/2018 | Faccioli et al. |
| 2018/0221537 A1 | 8/2018 | Johnson et al. |
| 2018/0236029 A1 | 8/2018 | Ting et al. |
| 2018/0243469 A1 | 8/2018 | Fathi et al. |
| 2018/0264172 A1 | 9/2018 | Yu et al. |
| 2018/0264175 A1 | 9/2018 | Kettenberger et al. |
| 2018/0280570 A1 | 10/2018 | Poundarik et al. |
| 2018/0326117 A1 | 11/2018 | Dang et al. |
| 2018/0344898 A1 | 12/2018 | Kronenthal et al. |
| 2019/0009004 A1 | 1/2019 | Liu et al. |
| 2019/0022273 A1 | 1/2019 | Hess et al. |
| 2019/0054196 A1 | 2/2019 | Koyakutty et al. |
| 2019/0091372 A1 | 3/2019 | Bhat et al. |
| 2019/0099522 A1 | 4/2019 | Preiss-Bloom et al. |
| 2019/0117842 A1 | 4/2019 | Nyemscek et al. |
| 2019/0125872 A1 | 5/2019 | Szymaitis |
| 2019/0134262 A1 | 5/2019 | Deng et al. |
| 2019/0142996 A1 | 5/2019 | Giannoudis et al. |
| 2019/0175734 A1 | 6/2019 | D'Agostino et al. |
| 2019/0175786 A1 | 6/2019 | Cohen et al. |
| 2019/0184056 A1 | 6/2019 | Jamal |
| 2019/0201451 A1 | 7/2019 | Paul et al. |
| 2019/0201584 A1 | 7/2019 | Zhang et al. |
| 2019/0290439 A1 | 9/2019 | Marionneaux et al. |
| 2019/0307921 A1 | 10/2019 | Morse et al. |
| 2019/0375149 A1 | 12/2019 | Linem et al. |
| 2019/0388585 A1 | 12/2019 | Wilson et al. |
| 2020/0000970 A1 | 1/2020 | Bagga et al. |
| 2020/0022814 A1 | 1/2020 | Touati et al. |
| 2020/0030065 A1 | 1/2020 | Touati et al. |
| 2020/0038547 A1 | 2/2020 | Ollila et al. |
| 2020/0054645 A1 | 2/2020 | Ellies et al. |
| 2020/0055853 A1 | 2/2020 | Ellies et al. |
| 2020/0069430 A1 | 3/2020 | Walker et al. |
| 2020/0069837 A1 | 3/2020 | Adkisson et al. |
| 2020/0086000 A1 | 3/2020 | Elian et al. |
| 2020/0093963 A1 | 3/2020 | Bagga et al. |
| 2020/0121463 A1 | 4/2020 | Yoshikawa et al. |
| 2020/0138907 A1 | 5/2020 | Oner et al. |
| 2020/0197571 A1 | 6/2020 | Johnson et al. |

* cited by examiner

BONE REPAIR COMPOSITION AND KIT

CROSS REFERENCE TO RELATED APPLICATIONS

This application is a continuation of and claims priority to U.S. Ser. No. 16/230,399 (the entire contents of which are incorporated herein by reference).

BACKGROUND

The repair of bone defects can be facilitated by placing a bone repair material as a temporary substitute at the site of the bone defect. Once placed, the bone repair material promotes and guides the regeneration of a natural bone structure.

Both naturally-derived and synthetically-produced bone repair materials can be used to repair bone defects. Naturally-derived materials include grafts made from bone. The bone may be harvested directly from the patient, as in autograft-based procedures, or it may be harvested from a suitable donor, surrogate, or cadaver, as in allograft- or xenograft-based procedures. However, autograft bone implant procedures are costly and cause additional discomfort for the patients, as they typically require an additional surgery for harvesting the graft material, which may cause significant morbidity at the donor site. Autografts may also show pronounced resorption making the outcome of the repair unpredictable.

Allogenic bone repair materials can also be used for bone repair, but their origin raises possible pathogenic transfers and ethical issues. Similar concerns are brought up against xenogenic graft materials. Alternatively, naturally-derived bone repair materials may be replaced by a completely synthetic bone repair material. Unfortunately, in contrast to naturally-occurring bone repair materials, synthetic bone repair materials are often less osteoconductive and are poorly osteoinductive.

While significant research has been carried out in the area of bone repair materials, there remains a need for improved bone repair materials that are biocompatible, durable, and effectively stimulate bone repair.

SUMMARY OF THE INVENTION

In one aspect, the present invention provides a bone repair composition. The composition includes a mixture of: a type I collagen; a type I collagen-glycosaminoglycan coprecipitate; tricalcium phosphate; and bioactive glass. In some embodiments, the tricalcium phosphate comprises particles having a size from 500 to 1400 microns. In some embodiments, the bioactive glass comprises particles having a size from 500 to 1000 microns. In some embodiments the bioactive glass comprises from 15% to 25% by weight, while in additional embodiments the tricalcium phosphate comprises from 75% to 85% by weight. In additional embodiments, the bioactive glass develops a hydroxyapatite surface layer upon implantation within a subject. In some embodiments, the bone repair composition exhibits a color change upon sterilization. In an additional embodiment, the bone repair composition is configured as a rectangular strip.

In additional embodiments of the bone repair composition, the glycosaminoglycan can be chondroitin 4 sulfate or chondroitin 6 sulfate. In some embodiments, the combined weight percent of the type I collagen and the type I collagen-glycosaminoglycan coprecipitate is from 1% to 5%. In further embodiments, the type I collagen-glycosaminogly- can coprecipitate comprises a ratio of glycosaminoglycan to type I collagen from between 1 to 10 and 1 to 12. In some embodiments the type I collagen in a ratio of about 1:1 compared with type I collagen-glycosaminoglycan coprecipitate. In additional embodiments, the type I collagen comprises fine flakes or particles obtained by milling collagen through a 20 mesh screen.

Another aspect of the invention provides a method of repairing a bone defect, comprising administering a bone repair composition as described herein to the site of the defect. For example, in some embodiments the composition is configured as a rectangular strip. In some embodiments, the composition is hydrated with autologous blood before administering the composition to the site of the defect. In some embodiments, the bone defect is, or is the result, a simple fracture, a compound fracture, external fixation, internal fixation, joint reconstruction, arthroplasty, degenerative disc disease, avascular osteonecrosis, osteosarcoma fracture, fracture non-unions, spinal fusion, disc augmentation, or bone regeneration in orthopedic implants.

Another aspect of the invention provides a bone repair kit. The bone repair kit includes a bone repair composition, comprising a mixture of: a type I collagen; a type I collagen-glycosaminoglycan coprecipitate; tricalcium phosphate; and bioactive glass; and a package for holding the bone repair composition. In some embodiments, the bone repair composition is configured as a rectangular strip. In some embodiments, the kit further comprising instructions for repairing a bone defect. In further embodiments, the packaging includes a tray configured to fit the shape of the bone repair composition. In yet further embodiments, the tray includes one or more grip regions to facilitate access to the bone repair composition. In some embodiments, the package comprises high density polyethylene.

DETAILED DESCRIPTION OF THE INVENTION

Figure 1:
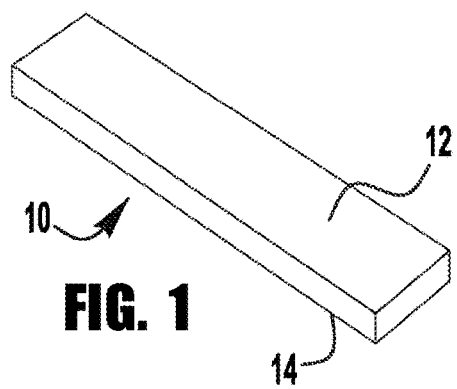
FIG. 1 provides a perspective view of a rectangular strip of the bone repair composition.
Figure 2A:
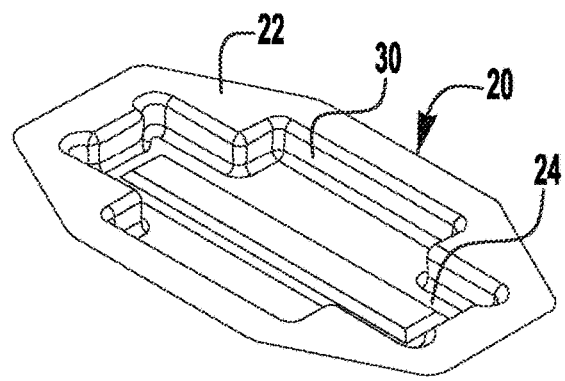
FIGS. 2A-2D provide drawings showing (A) a perspective view of the bone repair tray; (B) a top view of the bone repair tray; (C) a side view of the bone repair tray; and (D) a sectional view of the bone repair tray.
Figure 2B:
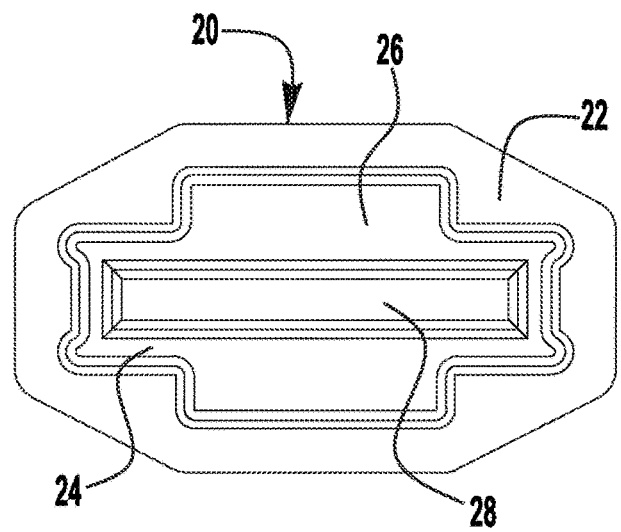
Figure 2C:
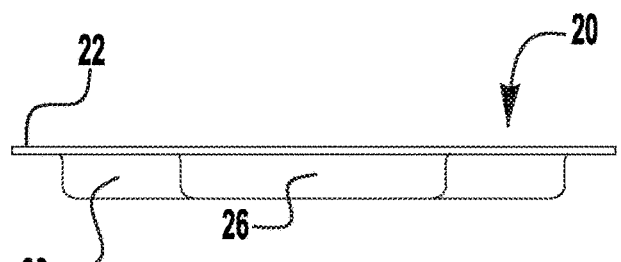
Figure 2D:
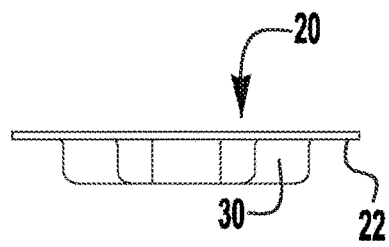
Figure 3A:
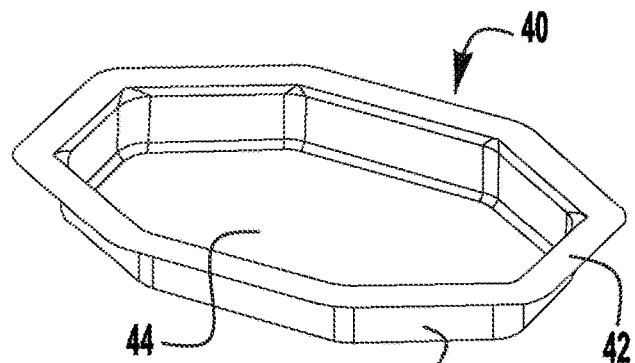
FIGS. 3A-3D provide drawings showing (A) a perspective view of the bone repair kit cover; (B) a top view of the bone repair kit cover; (C) a side view of the bone repair kit cover; and (D) a sectional view of the bone repair kit cover.
Figure 3B:
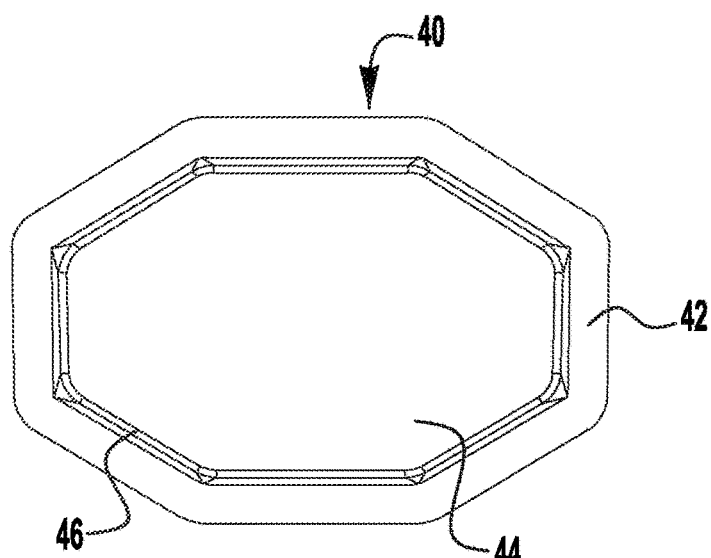
Figure 3C:
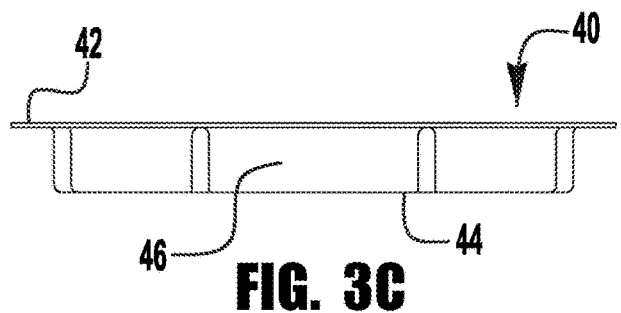
Figure 3D:
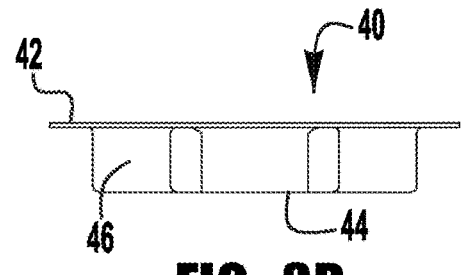

The present invention provides a biocompatible material for bone repair. The bone repair composition includes a mixture of a type I collagen, a type I collagen-glycosaminoglycan coprecipitate, tricalcium phosphate; and bioactive glass. Methods of using the composition for bone repair, and a kit for packaging the bone repair composition are also described.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "comprises," "comprising," "includes," "including," "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

A "subject," as used herein, can be any animal, and may also be referred to as the patient. Preferably the subject is a vertebrate animal, and more preferably the subject is a mammal, such as a research animal (e.g., a mouse or rat) or a domesticated farm animal (e.g., cow, horse, pig) or pet (e.g., dog, cat). In some embodiments, the subject is a human.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Biocompatible" as used herein, refers to any material that does not cause injury or death to a subject or induce an adverse reaction in a subject when placed in contact with the subject's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts at toxic concentrations, does not cause prolonged inflammation or irritation, or does not induce more than a basal immune reaction in the host.

As used herein, "treatment" means any manner in which the symptoms of a defect, condition, disorder, or disease, or any other indication, are ameliorated or otherwise beneficially altered.

Bone and Bone Repair

Long bones are composed of a dense outer cortical bone (also called compact bone), which encloses an irregular medullary space or cavity containing cancellous bone. The cortical bone is a dense and compact bone that generally has a higher mineral content than cancellous bone and higher stiffness and strength. The primary structural unit of the cortical bone is the osteon or haversian system, which is made up of cylindrical shaped lamellar bone that surrounds vascular channels called haversian canals. The outer cortical surface is enveloped in the periosteum, which is a connective tissue that contains blood vessels, sensory nerves and dense fibrous tissue and cells that maintain, change and repair the external cortical surface. The cancellous bone (also called spongy bone or trabecular bone) is composed of a branching network of interconnecting bony trabecular elements and contains cells that have osteogenic potential. Osteoprogenitor cells are present in the endosteum that lines the inner surface of the bone and covers the trabeculae of the cancellous bone, and also in the periosteum.

In response to injury, bone is able to regenerate and remodel to heal itself. For example, uncomplicated fractures are able to heal without surgical intervention in 6 months or less. The process of healing includes endochrondral or intramembranous ossification. In general, in response to injury, mesenchymal stem cells from the surrounding tissue migrate into the wound site and differentiate into cartilage or bone cells (i.e. osteoblasts). A typical sequence of events includes: hemorrhage; clot formation; dissolution of the clot with concurrent removal of damaged tissues; ingrowth of granulation tissue; formation of cartilage; capillary ingrowth and cartilage turnover; rapid bone formation (bony callus); and, finally, remodeling of the callus into cortical and trabecular bone. Bone repair, therefore, is a complex process that involves many cell types and regulatory molecules. The diverse cell populations involved in fracture repair include stem cells, macrophages, fibroblasts, vascular cells, osteoblasts, chondroblasts, and osteoclasts.

Bone Repair Compositions

One aspect of the present invention provides a bone repair composition. The bone repair composition includes a mixture of a type I collagen; a type I collagen glycosaminoglycan coprecipitate; tricalcium phosphate; and bioactive glass. A "composition," as used herein, refers to any mixture of materials. It can be a solid, suspension, powder, particulate, paste, or any combination thereof. In some embodiments, the composition is a solid particulate dispersion.

Collagen is the major protein component of bone, cartilage, skin, and connective tissue in animals. Collagen occurs in several types, having differing physical properties. The most abundant types are Types I, II and III. Collagen derived from any source is suitable for use in the compositions of the present invention, including insoluble collagen, collagen soluble in acid, in neutral or basic aqueous solutions, as well as those collagens that are commercially available. Typical animal sources for collagen include but are not limited to recombinant collagen, fibrillar collagen from bovine, porcine, ovine, caprine, avian, and shark sources as well as soluble collagen from sources such as cattle bones and rat tail tendon. In some embodiments, the collagen is obtained from corium, which is a base material from which collagen is extracted.

Type I collagen is the most abundant collagen of the human body which forms large, eosinophilic fibers known as collagen fibers. The COL1A1 gene produces the pro-alpha1 (I) chain. This chain combines with another pro-alpha1(I) chain and also with a pro-alpha2(I) chain (produced by the COL1A2 gene) to make a molecule of type I procollagen. Type I collagen is present in scar tissue, as well as tendons, ligaments, the endomysium of myofibrils, the organic part of bone, the dermis, the dentin and organ capsules.

The collagen included in the bone repair composition can be in the form of small flakes, particles, or fibers. Small flakes or particles can be obtained by milling a collagen sponge, or other form of collagen having a reticulated cellular structure. For example, in some embodiments, the collagen comprises fine flakes or particles obtained by milling collagen through a 10, 20, or 30 mesh screen. A preferred size is obtained by milling collagen through a 20 mesh screen.

The collagen is included in the bone repair composition both as type I collagen and as a type I collagen-glycosaminoglycan coprecipitate. In some embodiments, the ratio of type I collagen to type I collagen-glycosaminoglycan coprecipitate ranges from about 0.5:1 to about 2:1. In further embodiments, the ratio of type I collagen to type I collagen-glycosaminoglycan coprecipitate ranges from about 0.8:1 to about 1.5:1. In further embodiments, the type I collagen is present in a ratio of about 1:1 compared with type I collagen glycosaminoglycan coprecipitate.

The amount of type I collagen included in the bone repair composition can vary from about 0.5% to about 20% by weight. In some embodiments, the bone repair composition includes from 0.5% to 15% collagen by weight, in further embodiments, the bone repair composition includes from 0.5% to 10% collagen by weight, in yet further embodiments, the combined weight percent of the type I collagen and the type I collagen-glycosaminoglycan coprecipitate is from 1% to 5%, while in additional embodiments the bone repair composition includes an amount from 2% to 4% type I collagen, from the pure and co-precipitate forms of collagen, combined.

The bone repair composition also includes a type I collagen-glycosaminoglycan coprecipitate. The type I collagen-glycosaminoglycan coprecipitate is formed when collagen is precipitated from acid dispersion by addition of a GAG such as chondroitin 6-sulfate. The relative amount of GAG in the coprecipitate varies with the amount of GAG added and with the pH. Yannas et al., J Biomed Mater Res., 14(2):107-32 (1980). The coprecipitate is predominantly collagen. In some embodiments, the type I collagen glycosaminoglycan coprecipitate comprises a ratio of glycosaminoglycan to type I collagen from between 1 to 8 and 1 to 15. In further embodiments, the type I collagen glycosaminoglycan coprecipitate comprises a ratio of glycosaminoglycan to type I collagen from between 1 to 10 and 1 to 12. In some embodiments, the ratio is about 1 to 11.

The term glycosaminoglycan (GAG) describes hexosamine-containing polysaccharides. Glycosaminoglycans are also referred to as mucopolysaccharides. Chemically, GAG are alternating copolymers made up of residues of hexosamine that are glycosidically bound and alternating in a more or less regular manner with either hexuronic acid or hexose moieties. Glycosaminoglylcans can be obtained from various marine and mammalian sources.

Examples of glycosaminoglycan molecules that can be included in the bone repair composition include hyaluronic acid and chondroitin sulfate. Various forms of GAG which may be suitable for use in the bone repair composition include, but are not limited to, hyaluronic acid, chondroitin 6-sulfate, chondroitin 4-sulfate, heparin, heparin sulfate, keratin sulfate and dermatan sulfate. In some embodiments, the glycosaminoglycan included in the bone repair composition is chondroitin 4 sulfate or chondroitin 6 sulfate.

The bone repair composition also includes a bone growth stimulator (e.g., tricalcium phosphate). Typically, this is the main material included in the bone repair composition, by weight. In some embodiments, the bone growth stimulator (e.g., tricalcium phosphate) comprises from 60% to 95% by weight, from 65% to 90% by weight, from 70% to 90% by weight, from 75% to 85% by weight, or from 75% to 80% by weight.

Suitable bone growth stimulators include substances that can enhance bone repair. Some examples of bone growth stimulators include, but are not limited to, calcium, hydroxyapatite, tricalcium phosphate, chitosan, coral derivatives, bone growth factors, such as for example bone morphogenic proteins, and the like. Hydroxyapatite includes $Ca_{10}(PO_4)_6(OH)_2$, and is exogenous calcium phosphate that resembles the primary inorganic component of bone. This agent provides an osteophillic matrix for bone to bond and grow. A preferred bone growth stimulator for inclusion in the bone repair composition is tricalcium phosphate $(Ca_3(PO_4)_2)$. This term also includes sources or variants of tricalcium phosphate, such as bone ash, alpha or beta tricalcium phosphate, and combinations thereof.

The bone growth stimulator (e.g., tricalcium phosphate) is included in the bone repair composition as small particles. In some embodiments, the particles have a size from 250 to 2500 microns. In other embodiments, the particles have a size from 300 to 2000 microns. In further embodiments, the particles have a size from 400 to 1600 microns. In yet further embodiments, the particles have a size from 500 to 1400 microns. In additional embodiments, the particles have a size from 600 to 1200 microns.

The bone repair composition also includes bioactive glass. Bioactive glass is glass that is glass that undergoes specific surface reactions when implanted into a subject that facilitates integration and biocompatibility of the material. For example, in some embodiments the bioactive glass develops a hydroxyapatite surface layer upon implantation that facilitates the formation of a firm bond with hard and soft tissues. Bioactive glass is commercially available from companies such as Prosidyan® and the Mo-Sci Corporation. Bioactive glass is based on Silicon Dioxide ($SiO_2$) but also typically includes lesser amounts of Calcium Oxide (CaO), Sodium Oxide ($Na_2O$), and Phosphorus Pentoxide ($P_2O_5$). Embodiments of the bone repair composition can include varying amounts of the bioactive glass. In some embodiments, the bone repair composition includes from 10% to 98% bioactive glass by weight. In other embodiments, the bone repair composition can include 5% to 40% bioactive glass by weight. In other embodiments, the composition includes from 10% to 30% bioactive glass. In other embodiments, the composition includes from 15% to 25% bioactive glass, while in further embodiments, the composition includes from 18% to 23% bioactive glass. High levels of bioactive glass can be obtained by replacing ceramic material with bioactive glass.

The bioactive glass is included in the bone repair composition as small particles. In some embodiments, the bioactive glass particles have a size from 100 to 2000 microns. In other embodiments, the bioactive glass particles have a size from 250 to 1500 microns. In further embodiments, the bioactive glass particles having a size from 500 to 1000 microns.

The various materials included in the bone repair composition can be cross-linked to increase the stability of materials prepared using the bone repair composition. Collagen can be crosslinked using methods generally known in the art, such as by heat, radiation, or using conventional chemical crosslinking agents such as, for example, aldehydes, carbodiimides, epoxides, or imidazoles. One suitable chemical method for covalently cross-linking collagen/GAG matrices is known as aldehyde cross-linking. In this process, the materials are contacted with aqueous solutions of aldehyde, which serve to cross-link the materials. Suitable aldehydes include formaldehyde, glutaraldehyde and glyoxal. The preferred aldehyde is glutaraldehyde because it yields a desired level of cross-link density more rapidly than other aldehydes and is also capable of increasing the cross-link density to a relatively high level. When glutaraldehyde is used as the cross-linking agent, it is preferred that non-toxic concentrations of greater than about 0.25% be used.

Other chemical techniques that are suitable for increasing cross-link density in the present invention include carbodiimide coupling, azide coupling, and diisocyanate cross-linking.

The bone repair composition can further comprise bioactive molecules to facilitate bone repair or have other beneficial effects. Suitable bioactive molecules include, but are not limited to, growth factors, anti-inflammatory agents, wound healing agents, anti-scarring agents, antimicrobial agents (for example, silver), cell-adhesion peptides including Arg-Gly-Asp (RGD) containing peptides, nucleic acids, nucleic acid analogues, proteins, peptides, amino acids, and the like, or combinations thereof.

Pharmacologically active agents that can be included in the bone repair includes, for example, VEGF (vascular endothelial cell growth factor), FGF (the fibroblast growth factor family of proteins), TGFβ (transforming growth factor B), hepatocyte growth factor (HGF), platelet factor 4 (PF4), PDGF (platelet derived growth factor), EGF (epidermal growth factor), NGF (nerve growth factor), BMP (bone morphogenetic protein family), coagulation factors such as one of the vitamin K-dependent coagulant factors, such as Factor II/IIa, Factor VIINIIa, Factor IX/IXa or Factor X/Xa. Factor V/Va, VIIINIIIa, Factor XI/XIa, Factor XII/XIIa, Factor XIII/XIIIa, and mixtures thereof may also be used. Antibiotics, antifungal agents, hormones, enzymes, enzyme inhibitors, and mixtures thereof can also be incorporated in the compositions of the instant invention and subsequently delivered to the wound site.

The bone repair composition can be treated to sterilize or to reduce bioburden of the material. For example, sterilization procedures can include low dose irradiation, antibiotic washing and physical debridement. These methods provide the benefit of reducing antigenicity as well as sterilizing the bone repair composition. More extensive sterilization can be provided through gamma irradiation, electron beam irradiation, or ethylene oxide treatment.

In some embodiments, the bone repair composition exhibits a color change upon sterilization. For example, the bone repair composition, which is typically white or off-white in color, can darken to a gray or black upon exposure to irradiation (e.g., gamma irradiation). This demonstrates that sterilization has been effective, and can also indicate if the bone repair composition has subsequently been contaminated, which can shift the color back to white or off-white. This type of color change is mediated by the bioactive glass included in the bone repair composition.

The bone repair composition provides a biocompatible material that can be implanted at the site of a bone defect to facilitate bone repair. The shape and dimensions of the material can vary depending on the type of bone defect that is being repaired. For example, the bone repair composition can be configured as a sheet, a rod, a sphere, a tube, a cone, or a rectangular strip. FIG. 1 provides a perspective view of a rectangular bone repair composition strip 10, having a rectangular top surface 12 and sides 14. Furthermore, the shape of the bone repair composition can be modified immediately before use by cutting or trimming the bone repair material. In one embodiment, these dimensions may range from about 1 cm to about 1 meter in length, for example, from about 3 cm to about 8 cm in length, from about 0.5 mm to about 30 mm in thickness, for example, from about 2 mm to about 10 mm in thickness, and from about 0.05 mm to about 150 mm in width, for example, from about 2 mm to about 10 mm in width.

Methods of Bone Repair

In one aspect, the present invention provides a method of repairing a bone defect, comprising administering a bone repair composition to the site of the defect. The bone repair composition can be any of the bone repair compositions described herein.

The bone repair composition can be used to promote bone growth and/or bone remodeling, including in the treatment of any of a variety of bone diseases, disorders, defects or injuries for which other bone grafts, including allografts or autografts, have been employed. Such diseases, disorders, defects or injuries are well known to a skilled artisan. The subject for treatment can be any animal subject that has a bone disease, disorder, defect or injury and is in need of treatment, including any mammal, such as a human or non-human primate. In particular examples, the subject is a human. The bone repair composition can be used to fill or partially fill bone voids and/or gaps of the skeletal system associated with the bone disease, disorder, defect or injury.

For example, the bone repair compositions described herein can be used to correct bone defects in orthopedic, neurosurgical plastic or reconstructive surgery, in periodontal procedures, and in endodontic procedures. Such applications include, but are not limited to, induction of bone formation for hip replacement operations, knee replacement operations, foot and ankle surgeries (e.g. ankle fusion), spinal fusion procedures, repair of periodontal defects, treatment of osteoporosis, repair of bone tumor defects, dental procedures, repair of cranial maxilla facial defects and repair of bone fractures or defects. The bone disease, disorder, defect or injury can result from a developmental failure, or by degeneration or trauma, caused naturally or by surgery. Preferably the bone defect being repaired is not a load-bearing bone.

Non-limiting examples include repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterial cervical and thoracic operations, repair of spinal injuries, scoliosis, lordosis and kyphosis treatment, intermaxillary fixation of fractures, mentoplasty, temporomandibular joint replacement, alveolar ridge augmentation and reconstruction, inlay bone grafts, implant placement and revision or sinus lifts.

For example, bone diseases, disorders, defects, or injuries that can be treated with bone repair compositions provided herein include, but are not limited to, bone detects that include or are the result of a simple fracture, a compound fracture, external fixation, internal fixation, joint reconstruction, arthroplasty, degenerative disc disease, avascular osteonecrosis, osteosarcoma fracture, fracture non-unions, spinal fusion, disc augmentation, or bone regeneration in orthopedic implants.

The bone repair composition can be administered directly to the site of the bone disease, disorder, defect, or injury. In particular, the bone repair composition can be packed directly onto the site affected by the bone disease, disorder, defect, or injury. For example, the bone repair composition can be packed into bony voids. In some embodiments, the bone repair composition can be molded or formed into a desired shape generally conforming to the shape and size of the defect site, and then positioned or pressed, either manually and/or using instrumentation, into the defect site. For example, in some embodiments, the bone repair composition is configured as a rectangular strip. If necessary, a cover can be applied over the product where it has been applied or packed into bone.

In some embodiments, the bone repair composition is hydrated with a physiological solution before administering the bone repair composition to the defect. A physiological solution is one that contains a salt composition and osmotic pressure similar to blood plasma. In some embodiments, the physiological solution is autologous blood. There are several advantages associated with the use of autologous blood to hydrate the bone repair composition. First, it will be readily available during a bone repair procedure without requiring additional steps, and since it is fresh and from the subject undergoing bone repair it will not cause rejection, and will not require the use of stabilizers or anticoagulants. Second, autologous blood also provides useful blood components such as stem cells and growth factors in the appropriate physiological amounts, which can simulate and support the natural cascade of events involved in bone repair. Finally, the use of autologous blood will minimize the risk of infection during surgery.

In some examples, the bone repair composition can be used in conjunction with devices employed in the treatment of bone diseases, defects, disorders and injuries, such as, for example, orthopedic cage devices, ceramics or plates that can be employed in the spine or in bones to promote bone growth and fusion. Furthermore, the bone repair composition can be used in conjunction with an autologous bone graft. The bone repair composition also can be administered with antibiotic, antimycotic, or other anti-inflammatory agents. In some cases, the bone repair composition can be administered in combination with osteoinductive factors, such as BMP-2, BMP-7, and/or PDGF, or the patient's blood, platelet rich plasma (PRP) or bone marrow in order to enhance bone repair.

Bone Repair Kits

Another aspect of the invention provides a bone repair kit. The kit includes a bone repair composition, comprising a mixture of: a type I collagen; a type I collagen glycosaminoglycan coprecipitate; tricalcium phosphate; and bioactive glass; and a package for holding the bone repair composition.

In addition to the above components, the subject kits may further include (in certain embodiments) instructions for repairing a bone defect using the bone repair composition. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), hard drive etc., on which the information has been recorded. Yet another form of these instructions that may be present is a website address which may be used via the internet to access the information at a removed site.

Use of the kit described herein provides a number of advantages. The kit facilitates maintaining sterility and integrity of the bone repair material. In some embodiments, the kit includes an inner tray that supports the bone repair material while providing improved access to forceps or fingers for removing the bone repair material from the kit. The inner tray is preferably configured to provide a chair configuration to support the bone repair material. This facilitates hydration of the bone repair material using, for example autologous blood by providing a region where the bone repair material can be allowed to drain after having been soaked in a hydrating solution. Hydrating the bone repair material in autologous blood using an inner tray including a chair region helps avoid puddling or blockage of the blood, while encouraging equal distribution of the blood through the bone repair material. In some embodiments, the kit also includes an outer tray that helps deliver the inner tray and the bone repair material to the sterile surgery field.

As used herein, the term "package" refers to a solid matrix or material such as glass, plastic, paper, foil and the like capable of holding the bone repair composition. For example, in some embodiments, the package comprises high density polyethylene. Preferable the package is transparent in order to allow the bone repair composition to be viewed from outside the package. In some embodiments, the package includes a tray that includes one or more grip regions to facilitate access to the bone repair composition.

The kits may also comprise one or more container means for containing a sterile, pharmaceutically acceptable fluid or optional components. In some embodiments, the kit includes distinct container means for each component. In such cases, one container could contain, for example, the collagen particles, and the other container could include, for example, the physiologically acceptable fluid. The kit can also include a solution to formulate the matrix component, both components separately, or a pre-mixed combination of the components, into a more gelatinous form for application to the body. It should be noted, however, that components of a kit could be supplied in a dry form, which would allow for "wetting" upon contact with body fluids (e.g., autologous blood). Thus, the presence of any type of physiologically acceptable fluid is not a requirement for the kits of the invention.

In some embodiments, the packaging includes a tray configured to fit the shape of the bone repair composition. FIGS. 2A-2D provide drawings showing an example of a bone repair tray 20 configured fit the shape of a bone repair composition 10 provided as a rectangular strip, as shown in FIG. 1. The bone repair tray 20 includes a flat tray sealing region 22 that provides a surface that can be associated with or bonded to a flat sheet (e.g., a paper sheet, not shown) to seal the bone repair tray 20. The version of the bone repair tray 20 shown in FIG. 2 has a substantially octagonal circumference. The bone repair tray 20 includes a well region 24 that can hold fluid such as blood that can be used to moisten the bone repair composition 10 before use. The tray shown in FIG. 2 also includes two grip regions 26 that are positioned on either side of the bone repair composition 10 to facilitate gripping and withdrawing the bone repair composition 10 from the tray 20. The tray 20 can also include a support region 28 positioned in the middle of the well region 24 and between the grip regions 26 that supports the bone repair composition 10 above the bottom of the tray, which allows greater fluid access and easier withdrawal of the bone repair composition 10. The support region 28 can be configured to correspond to the shape of the bone repair composition 10, but slightly smaller so that the bone repair composition 10 will overhand the support region when placed in the tray 20. For example, when a rectangular bone repair composition 10 is used, the support region 28 will also be a rectangle having proportional dimensions, but slightly smaller. The tray 20 also include a tray wall 30 that extends from the tray sealing region 22 to the well region, thereby connecting the upper and lower portions of the tray 20.

The package used for the kit can also include a bone repair kit cover 40 that can be used to hold and protect the bone repair tray 20. FIGS. 3A-3D provide drawings showing an embodiment of the bone repair kit cover 40 having a substantially octagonal circumference that can be used to hold the bone repair tray 20 shown in FIG. 2. The bone repair kit 40 includes a flat cover sealing region 42 that runs around the circumference of the bone repair kit cover 40 that provides a surface that can be associated with or bonded to a flat sheet (e.g., a paper sheet, not shown) to seal the bone repair kit cover 40 with the bone repair tray 20 being sealed within. A cover wall 46 is perpendicular to the flat cover sealing region 42 and extends to a cover region 44, thereby forming a closed, dish shape with dimensions sufficient to allow the bone repair kit cover 40 to enclose the bone repair tray 20.

The kits of the invention may also comprise, or be packaged with, an instrument for assisting with the placement of the bone repair composition onto or within the body of an animal, for example, a mammal. Such an instrument may be a syringe, pipette, forceps, or any such medically approved delivery vehicle.

The present invention is illustrated by the following examples. It is to be understood that the particular examples, materials, amounts, and procedures are to be interpreted broadly in accordance with the scope and spirit of the invention as set forth herein.

EXAMPLES

Example 1: Process for Preparing Bone Repair Material

Figure 4:
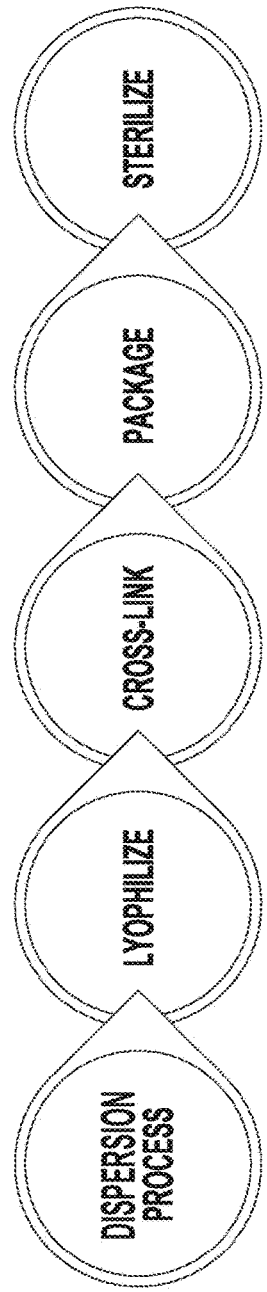
FIG. 4 provides a scheme showing the process flow for collagen strip preparation.

A production flow diagram showing the main steps in the production of collagen bone composite strips is provided by FIG. 4. To summarize, the process for preparing the bone repair composition includes the steps of adding collagen to acid; adding glycosaminoglycan to the collagen to form the GaG-collagen co-precipitate; adding tri-calcium phosphate and the bioactive glass to the collagen mixture; adding the mixture to a mold having the desired shape of the bone repair composition, freeze-drying the bone repair composition to remove water, cross-linking the composition, packaging the bone repair composition into a kit, and sterilizing the packaged bone repair composition.

Dispersion Process

Figure 5:
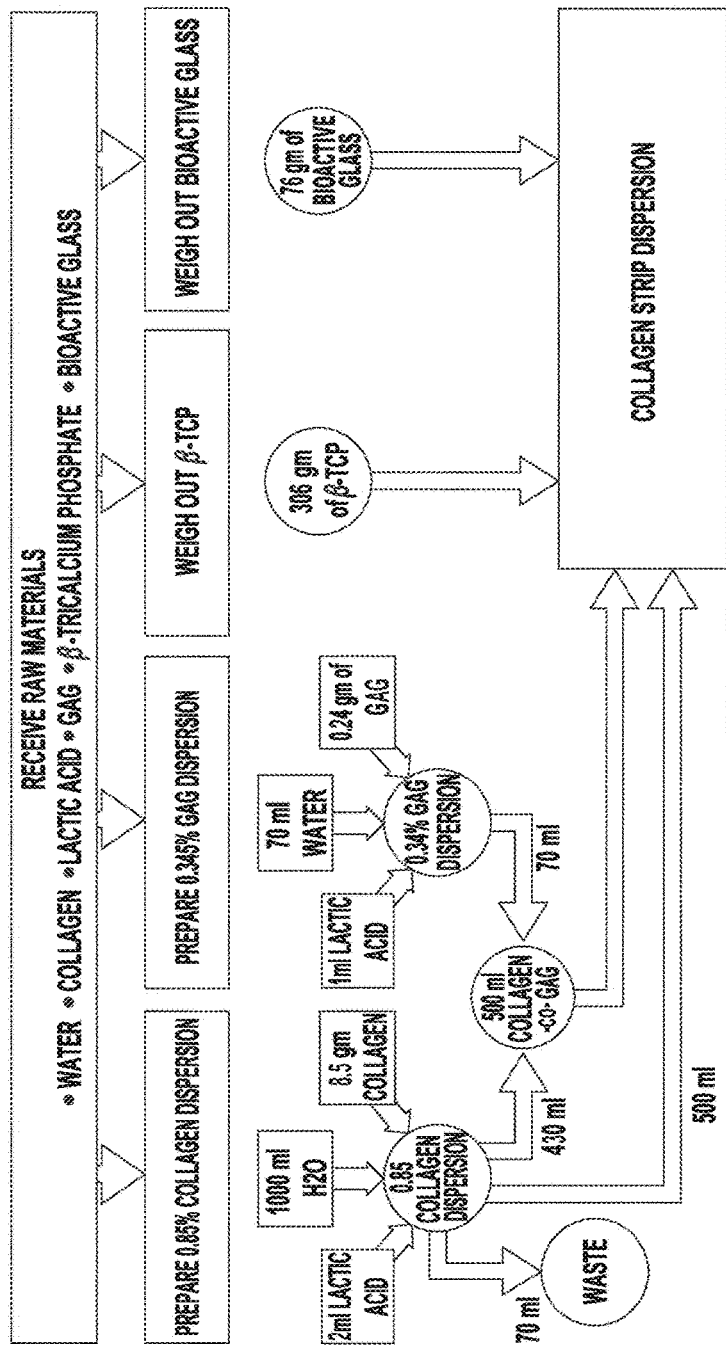
FIG. 5 provides a scheme showing the process flow outlining 1000 ml Collagen-co-GAG production through collagen strip dispersion.

During the dispersion process the desired outcome is two dispersions, a 0.85% collagen only (or "Neat) component and a 0.82% collagen dispersion co-precipitated with 0.023% glycosaminoglycan (GAG) (0.2415 gm/1070 ml). Following the flow diagram shown in FIG. 5, lots were made using the same raw materials and scaled to appropriate amounts. All material was received with a certificate of analysis (CofA) meeting the requirements of USP or "Certified for Human Use". Materials were measured out using a clean graduated cylinder (for liquids) and an OHAUS 4 place balance for solids. The initial collagen dispersion, containing 0.85% collagen, was made by mixing collagen, lactic acid, and ultrapure water in a large clean beaker. The material was hand stirred with a glass stir rod and allowed to rest in refrigerator (~4° C.) for 12-24 hours. Once "wetting" period is complete the mixture is dispersed using a Waring Blender at a speed of 3-5 k RPM for 3 minutes. The 0.85% dispersed collagen was divided out to 57% "Neat" and 43% used to make a collagen-co-GAG dispersion. The 0.345% GAG dispersion was created by dispersing GAG, lactic acid, and ultrapure water in a clean beaker.

Lyophilization

Once the collagen dispersion has been prepared, approximately 18.2 gm of the dispersion is poured into a 104.75 mm×21.78 mm×5.00 mm well of a hard coat anodized aluminum plate. Once all wells are full, each plate is placed in a −80° C. freezer for greater than 1 hour or until completely frozen. After the material is frozen each plate is moved into a pre-frozen lyophilizer (e.g., a Virtis™ lyophilizer). A 24-hour cycle is used to remove any water from the dispersion to leave a highly porous collagen/GAG/bioceramic strip Cross-Linking After the completion of lyophilization, the samples are removed from the mold using clean forceps and placed into a formaldehyde cross-linking chamber. An airstone placed in 10% formaldehyde solution is used to create a formaldehyde vaper into the chamber. This process is preferably run for about 1 to 2 hours. At the completion of this cycle, an airstone is activated in fresh water to provide humid air to outgas the samples, preferably for about 1 to 2 hours. Outgassing can be carried out using nitrogen flood or standard atmosphere with a relative humidity of 30 to 60%.

Packaging

Packaging consists of an inner and an outer thermoformed tray (FIGS. 2 & 3) with a sealed and labeled Tyvek lid on each tray. At the completion of outgassing, each sample is placed in an inner thermoformed tray. Each tray sealed with a breathable Tyvek lid using a 4-post pneumatic heat sealer. Before and after sealing of product occurred three samples were tested and passed for visual seal integrity. The inner trays were then labeled with labels.

Sterilization

The bone repair material should be sterilized before use. Preferably the bone repair material is sterilized using gamma irradiation. Gamma rays are a form of electromagnetic radiation, similar to x-rays but with a higher energy. Gamma rays can be obtained from radionuclide elements such as cobalt 60, which emit gamma rays during radioactive decay. Gamma rays can readily pass through the packaging of the kit and kill bacteria that may be present in the bone repair material by breaking the covalent bonds present in bacterial DNA. For sterilization of the bone repair material, preferably 25 to 40 kiloGrays of gamma irradiation are applied to the bone repair material within the plastic packaging of the kit.

The complete disclosure of all patents, patent applications, and publications, and electronically available materials cited herein are incorporated by reference. Any disagreement between material incorporated by reference and the specification is resolved in favor of the specification. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A bone repair composition, comprising
a particulate dispersion comprising a strip product and comprising a collagen component, a bone growth stimulator, and a bioactive glass,
wherein
the bioactive glass ranges from 15% to 25% by weight of the particulate dispersion and comprises bioactive glass particles having a size from 250 to 2000 microns,
the bone growth stimulator comprising calcium phosphate ranges from 75% to 85% by weight of the particulate dispersion and comprises bone growth stimulator particles having a size from 250 to 2500 microns, the collagen component ranges from 0.5% to 10% by weight of the particulate dispersion, and the strip product contains no hydroxyapatite in its formulation.

2. The composition of claim 1, wherein the bone growth stimulator particles have a size from 400 to 1600 microns.

3. The composition of claim 1, wherein the bioactive glass particles have a size from 250 to 1500 microns.

4. The composition of claim 1, wherein the bioactive glass develops a hydroxyapatite surface layer upon implantation within a subject.

5. The composition of claim 1, wherein the particulate dispersion is configured as a rectangular strip.

6. The composition of claim 1, wherein the collagen component is blended into an aqueous dispersion before incorporation into the particulate dispersion.

7. The composition of claim 6, wherein the particulate dispersion comprises a cross-linked dispersion formed from the aqueous dispersion of the collagen compound.

8. The composition of claim 7, wherein the cross-linked dispersion is formed from the aqueous dispersion mixed with the bioactive glass and the bone growth stimulator, freeze-dried, and then cross-linked.

9. The composition of claim 1, wherein the collagen compound comprises a type I collagen.

10. The composition of claim 9, wherein the collagen compound further comprises a type I collagen-glycosaminoglycan coprecipitate.

11. A method of repairing a bone defect, comprising administering a composition according to claim 1 to the site of the bone defect.

12. The method of claim 11, wherein the composition is hydrated before administering the bone repair composition to the site of the bone defect.

13. The method of claim 11, wherein the bone repair composition is hydrated with autologous blood.

14. The method of claim 11, wherein the bone defect is, or is the result, a simple fracture, a compound fracture, external fixation, internal fixation, joint reconstruction, arthroplasty, degenerative disc disease, avascular osteonecrosis, osteosarcoma fracture, fracture non-unions, spinal fusion, disc augmentation, or bone regeneration in orthopedic implants.

15. A bone repair kit, comprising:

the bone repair composition of claim 1; and a packaging including a tray for holding the bone repair composition, wherein the tray includes a support region having a raised surface above a bottom of the tray, and the raised surface holds the bone repair composition above the bottom of the tray.

16. The bone repair kit of claim 15, wherein the bone repair composition is configured as a rectangular strip.

17. The bone repair kit of claim 15, wherein the tray is configured to fit the shape of the bone repair composition.

18. The bone repair kit of claim 17, wherein the tray includes one or more grip regions to facilitate access to the bone repair composition.

19. The bone repair kit of claim 15, wherein the kit includes a cover that can be sealed with a sheet to hold the tray.

20. The bone repair kit of claim 15, wherein the package comprises high density polyethylene.

21. A bone repair composition, comprising a particulate dispersion comprising a strip product and comprising a collagen component, a bone growth stimulator, and a bioactive glass, wherein the bioactive glass ranges from 15% to 25% by weight of the particulate dispersion and comprises bioactive glass particles having a size from 250 to 2000 microns, the bone growth stimulator ranges from 75% to 85% by weight of the particulate dispersion and comprises bone growth stimulator particles having a size from 250 to 2500 microns, the collagen component ranges from 0.5% to 10% by weight of the particulate dispersion and comprises particles or flakes which are milled to pass through a 2000 micron mesh, and the strip product contains no hydroxyapatite in its formulation.

* * * * *